Nov. 4, 1975
R. S. MOORE
MINIATURE ROSE PLANT
Filed Dec. 9, 1974
Plant Pat. 3,800
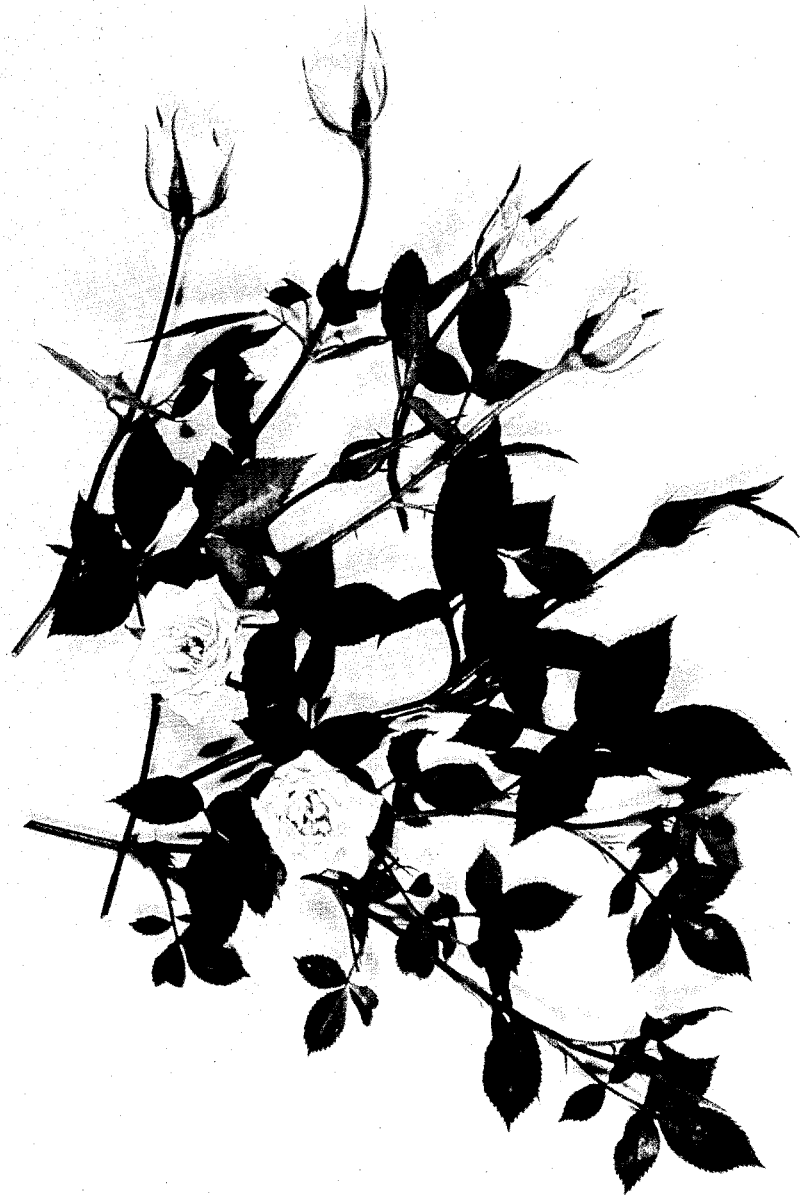

United States Patent

Plant Pat. 3,800

Patented Nov. 4, 1975

3,800

MINIATURE ROSE PLANT

Ralph S. Moore, 2519 E. Noble Ave.,
Visalia, Calif. 93277

Filed Dec. 9, 1974, Ser. No. 530,723

Int. Cl. A01h 5/00

U.S. Cl. Plt.—8 1 Claim

ABSTRACT OF THE DISCLOSURE

The present invention relates to a new and distinct variety of hardy, dwarf, bush type rose plant of the miniature class; the variety being primarily characterized—as to novelty—by soft yellow buds and flowers which in general color effect are light yellow, similar in color to Yellow Necklace (miniature—not patented).

The variety is further characterized by:

An abundance of bloom, with flowers borne singly or several to the stem in loose clusters.

Sweet fragrance (moderate).

A plant which is vigorous, of rounded spreading shape and with small medium green foliage with pointed leaflets; the buds and flowers being similar in form, but smaller in size, to Yellow Doll (miniature—Plant Pat. 2,450). The plant, which has a normal height of 12 to 16 inches can easily be maintained at lesser height by occasional trimming.

A plant which grows and blooms satisfactorily both in greenhouse and outdoors; is good for growing in pots; and provides excellent garden decoration as well as cut flowers.

The present variety of minature rose was originated by me at my nursery located at Visalia, Calif., under conditions of careful control and observation, as a cross between Golden Glow (Plant Pat. 263, expired) as the seed parent and an un-named seedling (Little Darling, Plant Pat. 1,581 (expired) × un-named red miniature seedling) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers: Continuity; Continuous—repeat bloom all season. Fragrance; Very little.

Flowers borne: Singly and several together on strong, medium length stems.

Quantity of bloom: Abundant both outside and in greenhouse.

Bud: Peduncle—medium to long; slender but sturdy; erect; medium green, sometimes tinted bronze. Hairs—numerous very fine soft hairs. Before calyx breaks; size—small. Form medium long; pointed; with a few foliaceous appendages and usually no hairs on surface of bud; with foliaceous parts extending beyond the tip of the bud equal to one half or more of its length. Color—medium green, sometimes tinted reddish or bronze. As calyx breaks; color—light yellow. As first petal opens; same general color; size small.

Bloom: Size when fully open—small, averaging about 1⅜" (3.5 cm.). Petalage—double, 30–35 petals (plus several small petaloids) arranged regularly. Form—slightly cupped at first, becoming more open; petals rolled loosely outward.

Petals: Fairly thick; satiny on both inside and outside. Shape—outside petals, broad lanceolate (almost round). Intermediate—broad lanceolate with acute tip. Inside—lanceolate with acute tip.

Color: Newly opened flower from a plant grown in cool plastic greenhouse (November 1974), Visalia, Calif.

*Outside petal.*—Outside surface—Sulphur Yellow 1/3, shading into Sulphur Yellow 1/2 (plus a greenish tint) on lower one-third of petal; inside surface—Sulphur Yellow 1/3, shading into Sulphur Yellow 1/1 on lower one-fourth of petal.

*Intermediate petal.*—Outside surface—Sulphur Yellow 1/3, blending into Sulphur Yellow 1/1 on lower one-half of petal; inside surface—Sulphur Yellow 1/3 blending into Sulphur Yellow 1/1 on lower one-third of petal.

*Inner petal.*—Outside surface—Sulphur Yellow 1/2 blending into Sulphur Yellow 1/1 on lower one-fourth of petal. Inside surface—Sulfur Yellow 1/2 blending into Sulphur Yellow 1/1 on lower one-fourth of petal. General color effect of newly opened flowers—soft or light yellow. Three days open—lighter yellow shade. Behaviour—as flowers age color becomes lighter shade before petals drop off. Flower longevity (September 1974)—bush in garden or pot, 4 to 5 days or longer. Cut flowers at living room temperature 4 to 5 days.

Reproductive organs:

*Stamens.*—Average, arranged fairly regularly about pistils; sometimes mixed with petaloids.

*Filaments.*—Short to medium; yellow.

*Anthers.*—Yellow.

*Pollen.*—Scarce.

*Pistils.*—Average number.

*Styles.*—Fairly even; bunched; color—reddish.

*Stigma.*—Color, off-yellow.

*Ovaries.*—All enclosed in calyx.

*Hips.*—None.

*Sepals.*—Long, recurved.

*Seeds.*—None.

Foliage:

*Leaves.*—Compound of five leaflets, sometimes seven; abundant; moderately small; leathery.

*Leaflets.*—Shape: Lanceolate; apex acute; base less acute. Margin serrate. Color: Normal green; new growth—reddish. Rachis: Long, narrow width; medium length; narrow points. Stipules: Long; narrow width; medium length; narrow points which may turn out at an angle of more or less than 45 degrees then curve inward (curbed).

Growth:

*Habit.*—Dwarf; bushy; rounded; much branched.

*Growth.*—Free; vigorous.

*Canes.*—Medium; slender.

*Main stems.*—Color: Medium green. May darken with age. Thorns: Average number; medium length; nearly straight (not curved) but inclined slightly downward; color: brown to gray. Prickles: None. Hairs: None.

*Branches.*—Color: Medium green. Thorns: Average thorny; medium length; slender; inclined slightly downward. Long oval base. Prickles: None. Hairs: None.

*New shoots.*—Color: Medium green to reddish. Thorns: Average number; medium length; slender, nearly straight; inclined slightly downward; sharp points; base oval. Prickles: None. Hairs: None.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, relatively dwarf, rounded, much branched, bush-type, as illustrated and described, characterized by buds and flowers resembling the Yellow Doll (Plant Pat. 2,450) miniature rose in general form of bud and flower, the color being a lighter shade of yellow and the petals tending to be broader and less numerous; the general color effect being soft yellow—of a shade resembling the Yellow Necklace miniature rose (not patented); and further characterized by a plant which is vigorous in growth but more compact in habit than Yellow Doll, easy to propagate from cuttings; with small medium green foliage, often tinted reddish on new growth; with flowers borne singly or several to stem.

No references cited.

ROBERT E. BAGWILL, Primary Examiner